United States Patent [19]

Hargis

[11] 4,029,707

[45] June 14, 1977

[54] PREPARATION OF N-ALKYLATED AROMATIC AMINES

[75] Inventor: Charles W. Hargis, Johnson City, Tenn.

[73] Assignee: Eastman Kodak Company, Rochester, N.Y.

[22] Filed: Sept. 2, 1975

[21] Appl. No.: 609,125

[52] U.S. Cl. .............................. 260/577; 260/576; 252/434; 252/441

[51] Int. Cl.$^2$ ........................................ C07C 87/62

[58] Field of Search ........... 260/577, 576; 252/441, 252/434

[56] References Cited

UNITED STATES PATENTS

| | | | |
|---|---|---|---|
| 2,115,884 | 5/1938 | Schollkopf | 260/577 |
| 3,222,400 | 12/1965 | Suter et al. | 260/577 |
| 3,267,146 | 8/1966 | Schmerling | 260/577 |
| 3,542,694 | 11/1970 | Schwettmann | 260/577 X |
| 3,941,844 | 3/1976 | Szymanski et al. | 260/576 X |
| 3,957,874 | 5/1976 | Dockner et al. | 260/577 |
| 3,969,411 | 7/1976 | Schneider | 260/576 X |

OTHER PUBLICATIONS

Lobanova et al., CA 77:5076d, (1972).
Lobanova et al., CA 77:74919t, (1972).
Parera et al., CA 70:11240z, (1969).
Standard Oil, CA 46:9834e, (1952).

*Primary Examiner*—Daniel E. Wyman
*Assistant Examiner*—Thomas A. Waltz
*Attorney, Agent, or Firm*—Elliott Stern; Daniel B. Reece, III

[57] ABSTRACT

N-Alkylated aromatic amines are produced in high yield by the vapor-phase reaction of an aromatic amine with a lower aliphatic alcohol at elevated temperature in the presence of an acidic agent supported on eta-alumina.

4 Claims, No Drawings

PREPARATION OF N-ALKYLATED AROMATIC AMINES

This invention relates to the N-alkylation of aromatic amines with an aliphatic alcohol. More particularly, this invention relates to the continuous N-alkylation of aromatic amines by the catalyst vapor-phase reaction of an aromatic amine with a lower aliphatic alcohol having from 1 to about 6 carbon atoms at elevated temperatures in the presence of a catalyst consisting of an acidic agent selected from hydrofluosilicic acid-and silicon tetrafluoride-treated eta-alumina to produce N-alkylated aromatic amines in high yield and purity.

A wide variety of methods have been proposed for preparing the N-alkyl and N,N-dialkyl derivatives of aromatic amines using a wide variety of catalysts. See for example U.S. Pat. Nos. 2,391,139, 2,813,124, 3,222,400, Canadian Pat. No. 492,022 and British Pat. No. 577,901. Although these several methods for preparing alkylated aromatic amines work to some extent, none of the vapor-phase methods proposed have proven to be particularly attractive from a commercial standpoint.

In accordance with this invention there is provided a process for the N-alkylation of an aromatic amine having at least one hydrogen atom attached to the amino nitrogen which comprises contacting a reaction mixture of a lower aliphatic alcohol and the aromatic amine in the vapor-phase at an elevated temperature in the presence of a catalyst comprising eta-alumina treated with an acid selected from silicon tetrafluoride or hydrofluosilicic acid. Both catalysts of the present invention promote a high and selective conversion of aromatic amines to their N-alkyl and N,N-dialkyl derivatives with an aliphatic alcohol. As used herein, the expression "lower aliphatic alcohol" refers to a straight or branched chain alcohol having 1 to about 6 carbon atoms.

Examples of aromatic amines which may be alkylated by the process of this invention are aniline, o-, m-, or p-toluidine, o-m-, and p-xylidine, o-, m-, and p-anisidine α- and β-naphthylamines, any other e.g., naphthalene amines, and the like. Suitable alkylating alcohols useful in the process of this invention are methanol, ethanol, butanol, isopropanol, pentanol and the like. In a preferred embodiment of this invention the aromatic amine is m-toluidine and the alcohol used is ethyl alcohol, the product being a combustion of N-ethyl- and N,N-diethyl-m-toluidine. The process of this invention provides the desired product in high chemical and space-time yields.

The mechanics of the process consist of contacting the reactants of the aromatic amine and aliphatic alcohol with the selected catalyst of this invention in the reaction zone at a temperature between about 250° to about 450° C. The process may be effected in a batch, intermittent, or continuous manner. However, since the reaction is carried out in the vapor-phase, and since it is necessary to maintain the reactants at the reaction temperature for a predetermined limited period of time, it is generally preferred to carry out the process in a continuous manner in which case the starting materials may be vaporized in a separate chamber of the front section of the reaction chamber and then passed through the reaction zone at the optimum temperature and the desired space velocity. As an alternative, the liquid reactants may be vaporized in the reaction chamber proper.

The process of this invention can be carried out in any type of reactor used for vapor-phase reaction in which the reactants and catalysts are brought into intimate contact for a sufficient length of time to accomplish the desired reaction. For example, a conventional fixed-bed tubular reactor, a fluidized bed reactor, or a moving bed reactor may be employed. It is generally preferred to employ a tubular reactor; for example, a glass or metal tube which is filled with a static bed of the catalyst. The reactor can be heated by any conventional means such as, for example, by surrounding the reactor with an electrical heater, a heated gas, or a liquid such as a fused salt bath, liquid metal, etc., which can be conveniently maintained at the reaction temperatures by use of an immersion-type electrical heater. Because of the good heat transfer between the liquid and the reactor walls a fused salt bath or other liquid medium generally gives the best temperature control of the reaction although any means of heating may be used.

The process is operable within a wide range of temperature, pressure, and contact times. However, because of sensitivity of organic compounds with changes in temperature under the reaction conditions, consideration must be given to the relation of operating variables. For instance, the permissible range of contact time will be different at various temperatures within the preferred temperature range. With increase in temperature, the contact time must be decreased commensurately to avoid excessive consumption of organic feed stock in side reactions. The optimum contact time will be a function of the organic reactants and catalysts chosen and of the reaction temperature, but will usually fall within the range of from 0.1 to about 20 seconds. The term "contact time" as used herein is defined as the time required for the gaseous feed mixture to fill a volume equal to the bulk volume of the catalyst at the temperature and pressure employed in the process. Although the reaction variables such as contact time, reaction temperature, and composition of the reactor feed mixture may be varied widely to obtain a wide degree of control over the composition of the alkylate product while maintaining high and selective conversions of the reactants, care must be exercised to avoid reaction temperatures so high as to result in excessive dehydration of the feed alcohol with consequent lowering of its effective use in the alkylation reaction. Within wide limits as the temperature is increased a commensurate decrease in the time of exposure of the reactants to the reaction zone will eliminate or lessen the occurrence of undesirable side reactions. The reaction conditions selected for optimum production of alkylate will depend, of course, on the particular aromatic amine to be alkylated, the alcohol employed and the desired composition of the reaction product.

The pressure at which the process is operated is not narrowly critical and can range from subatmospheric pressure to superatmospheric pressure in addition to normal atmospheric pressure. Since the reaction of this invention proceeds smoothly at atmospheric pressure thereby eliminating the need for overly expensive equipment which is required for operations carried out at other pressures, the process of this invention is preferably carried out at atmospheric pressure for economic reasons.

The reaction temperature may be varied between about 250° C. and 450° C. depending upon the selection of the catalyst used, the degree of conversion desired and the composition of the product to be obtained. At temperatures below about 250° C., the reaction time of the process increases to such a degree that it is no longer of commercial interest. Temperatures below about 250° C. are generally not acceptable. Temperatures above 450° C. are to be avoided because of the excessive decomposition of the reactants and products and the carbonization of the catalyst with resulting loss of its activity. It is preferred that the process of this invention be conducted at a temperature range from about 275° C. to about 350° C.

In some cases it may be desirable or even advantageous to employ an inert diluent or solvent in admixture with the reactants for the purpose of, for example, equalizing the temperature of the reaction zone, promoting a more uniform reaction rate, metering the reactant into the reaction zone, restricting the amount of undesirable side reactions and even for the purpose of increasing the catalyst life. Preferably, it is advantageous to dilute the vapor stream with nitrogen or other inert gas to aid in controlling the temperature in the reaction zone, to reduce the rate of side reactions, and to facilitate removal of reaction products from the reaction zone. The optimum ratio of the volume of diluent gas per volume of organic will depend upon the reactant being used and the reaction temperature and contact time but will usually be within the range of from 0 to 2.0, volumes inert gas per volume of organic vapor.

The molar ratio of alcohol to aromatic amine reactants can be varied from less than unity to about 10:1 to give the desired admixture of N-alkylated amine. At intermediate ratios of the reactant varying amounts of monoethyl m-toluidine and diethyl m-toluidine are produced and may be controlled within limits by adjusting temperature of reaction and/or the ratio of alcohol to aromatic amine in the feed. Little advantage is realized in the use of molar ratios of alcohol to aromatic amine higher than about 10:1 since little improvement in the production of product is gained at higher ratios.

The reaction products which are in the form of vapor from the reactor are collected, condensed and separated in any known manner such as, for example, by distillation. Since the reaction is preferably run at atmospheric pressure, no expensive pressure equipment is normally needed for the collection and separation of the reaction products. To achieve maximum yields it is desirable for any reactant which is passed through the reaction zone unchanged to be collected and recycled.

The catalysts which are employed in this process are an eta-alumina based catalyst which has been prepared by the treatment of eta-alumina with a specific acidic activating agent selected from silicon tetrafluoride or hydrofluosilicic acid. The alumina support may be in the form of extrusions, tablets, spheres, pellets, granules or other shape and of such particle size as to make it suitable for use in the design of the reactor employed. Eta-alumina is known in the art (see the technical paper entitled "Alumina Properties — Technical Paper No. 10" (second revision) published by the Aluminum Company of America, 1960) and can obtained either commercially or prepared according to the process described in U.S. Pat. No. 3,249,557. The catalyst used may be prepared by in situ treatment of a reactor charge of extrusions of eta-alumina with silicon tetrafluoride at a temperature of about 350° C. When no further reaction with the support occurs as evidenced by the disappearance of the hot spot in the reactor which traversed the length of the catalyst bed as the reaction proceeded, the catalyst may then be flushed with nitrogen as the temperature is changed to the testing temperature. In another aspect of this invention the catalyst may be prepared by allowing eta-alumina to soak overnight at ambient temperature in a water solution containing hyrofluosilicic acid. After draining of the excess liquid the eta-alumina extrusions may be dried at about 125° C. and then heated at 450° C. for about 3 hours to complete the catalyst preparation.

The invention will be further illustrated by the following examples.

Experiments were carried out in a 1-in. O.D. "Vycor" tubular reactor 33 in. long and heated by a three-element electric furnace equipped with automatic temperature control. A 50-ml. charge of the catalyst was supported on a bed of Vycor cullet in the reactor; a bed of Vycor cullet above the catalyst served as a preheat section. Temperatures inside the reactor were measured by a movable thermocouple in a coaxially-mounted thermocouple well. Liquid reaction product was collected by passing the reactor effluent through receivers cooled to 10° C. and — 80° C. Analysis of product samples was by gas-liquid chromatography. Experimental results were calculated on a mole basis as follows:

$$\text{Percent conversion} = \frac{\text{moles of specified product} \times 100}{\text{moles of m-toluidine fed}}$$

$$\text{Percent yield} = \frac{\text{moles of specified product} \times 100}{\text{moles of m-toluidine consumed}}$$

Table 1 shows results obtained under various testing conditions by analysis of liquid product. Wide flexibility in controlling the composition of alkylated product is demonstrated to result from changes in reaction variables such as feed composition and contact time as reflected by changes in production values and molar ratios of alkylated product components.

EXAMPLES 1–3

N-Ethylation of m-Toluidine Over eta-Alumina-based Catalysts

The catalyst of Example 1 was prepared by in situ treatment of a 50-ml. reactor charge of ⅛-in. extrusions of eta-alumina with silicon tetrafluoride at a temperature of 350° C. When no further reaction with the support occurred as evidenced by the disappearance of a hot spot which traversed the length of the catalyst bed as reaction proceeded, the catalyst was flushed with nitrogen as the temperature was lowered to the testing temperature of Example 1.

The catalyst of Examples 2 and 3 was prepared as follows: A mass of 60 g. of eta-alumina in the form of ⅛-in. extrusions was allowed to soak overnight at ambient temperature in 200-ml. of a distilled water solution containing 22.25 g. of 30% hydrofluosilicic acid. After draining off the excess liquid, the extrusions were dried at 125° C. and then heated at 450° C. for 3 hr. to complete the catalyst preparation. The results obtained on testing the catalysts are shown in Table I.

The results indicate that the hydrofluosilicic acid treatment of the alumina support gave a more active catalyst (Examples 2 and 3) than obtained by the silicon tetrafluoride treatment (Example 1) as shown by the higher conversions to alkylated product components in Example 2 and 3.

Table I

| Example No. | Molar Ratio Reactants ETOH:m-toluidine | Time, Min. | Temp. °C. | Contact Time Sec. | Production of N-Ethyl m-Toluidines | | | | Molar Ratio MEMT/DEMT* |
|---|---|---|---|---|---|---|---|---|---|
| | | | | | Monoethyl Toluidine | | Diethyl Toluidine | | |
| | | | | | Conv. % | Yield, % | Conv. % | Yield, % | |
| 1 | 4:1 | 150 | 275 | 8.85 | 51.7 | 84.0 | 6.6 | 10.8 | 7.87 |
| 2 | 4:1 | 255 | 275 | 8.85 | 58.4 | 76.6 | 14.2 | 20.3 | 3.78 |
| 3 | 4:1 | 155 | 325 | 2.22 | 61.7 | 80.0 | 14.4 | 18.6 | 4.27 |

*MEMT = Monoethyl-m-toluidine
DEMT = Diethyl-m-toluidine

EXAMPLE 4

The experiment of Example 2 is repeated except the aromatic amine is aniline. Collection and analysis of the product shows the production of N-ethylated anilines in high conversion and yield.

EXAMPLE 5

The experiment of Example 2 is repeated except the aromatic amine is aniline and the alkylating alcohol is isopropyl alcohol. Collection and analysis of the product as before shows the production of N-isopropylated anilines in high conversion and yield.

EXAMPLE 6

The experiment of Example 2 is repeated except the aromatic amine is aniline and the alcohol is methyl alcohol. Collection and analysis of the reaction product shows the production of N-methylated anilines in high conversion and yield.

EXAMPLE 7

Table II shows the beneficial results obtained using as a catalyst 50 ml. of eta-alumina treated with $H_2SiF_6$ as compared with the use of untreated eta-alumina. The alumina base utilized in both instances is Kaiser Ka-201. The $H_2SiF_6$-treated catalyst was prepared as in Examples 2 and 3.

Table II

| Run No. | Temp. °C. Furnace/Hot Spot | Time, Hr. Period/Total | C.T.[1] Sec. | Mole Ratio EA/MT[2] | Feed Comp. Wt. % | | Feed, Grams/Period | Product, Grams/Period | Monoethyl m-Toluidine | | Diethyl m-Toluidine | | MEMT[3]+ DEMT Prod'ty lb/ft³-hr. | MEMT/ DEMT, Wt. Ratio |
|---|---|---|---|---|---|---|---|---|---|---|---|---|---|---|
| | | | | | MT | EA | | | Conv. % | Yield % | Conv. % | Yield % | | |
| Catalyst - 50 ml. of Kaiser KA-201 eta-alumina treated with $H_2SiF_6$ | | | | | | | | | | | | | | |
| 1 | 325/335 | 8/8 | 2.2 | 2 | 53.8 | 46.2 | 866 | 821 | 46 | 63 | 11 | 16 | 56 | 3.4 |
| 2 | 325/335 | 8/16 | 2.2 | 2 | 53.8 | 46.2 | 865 | 828 | 51 | 70 | 14 | 19 | 62 | 3.0 |
| 3 | 325/335 | 8/24 | 2.2 | 2 | 53.8 | 46.2 | 865 | 830 | 53 | 73 | 15 | 19 | 65 | 2.8 |
| 5 | 325/335 | 8/40 | 2.2 | 2 | 53.8 | 46.2 | 865 | 834 | 53 | 73 | 16 | 22 | 66 | 2.7 |
| 8 | 325/335 | 8/64 | 2.2 | 2 | 53.8 | 46.2 | 866 | 802 | 41 | 48 | 18 | 21 | — | — |
| 10 | 325/335 | 8/80 | 2.2 | 2 | 53.8 | 46.2 | 867 | 824 | 53 | 68 | 16 | 21 | 66 | 2.7 |
| Catalyst - 50 ml. untreated Kaiser KA-201 eta-alumina | | | | | | | | | | | | | | |
| 1 | 325/332 | 8/8 | 2.2 | 2 | 53.8 | 46.2 | 867 | 858 | 43 | — | 4 | 12 | 43 | 9.7 6.7 |
| 5 | 325/332 | 8/40 | 2.2 | 2 | 53.8 | 46.2 | 865 | 843 | 39 | 89 | 4 | 8 | 42 | 10.6 6.7 |
| 8 | 325/332 | 8/64 | 2.2 | 2 | 53.8 | 46.2 | 864 | 825 | 40 | 92 | 4 | 9 | 41 | 8.8 6.7 |
| 10 | 343/350 | 8/76 | 3.0 | 2 | 53.8 | 46.2 | 651 | 658 | 60 | — | 7 | 14 | 45 | 7.0 |
| 12 | 343/350 | 8/84 | 3.0 | 2 | 53.8 | 46.2 | 651 | 602 | 51 | 85 | 6 | 10 | 42 | 7.0 |
| 13 | 343/350 | 8/92 | 3.0 | 2 | 53.8 | 46.2 | 648 | 598 | 52 | 85 | 6 | 10 | 42 | 7.0 |

[1]Contact time.
[2]EA = ethyl alcohol
MT = m-toluidine
[3]MEMT = monoethyl m-toluidine
DEMT = diethyl m-toluidine

EXAMPLE 8

Table III further illustrates the continuous production of m-toluidine over a period of 184 hours using the same catalyst as prepared in Examples 2 and 3. The reactor feed contained 3.3% by weight of water. The results indicate that the ethyl alcohol utilized need not be anhydrous for the successful operation of the process.

Table II

| Run No. | Temp. °C. Furnace/Hot Spot | Time, Hr. Period/Total | C.T. Sec. | Mole Ratio EA/MT | Feed Comp. Wt. % | | | Feed, Grams/Period | Product Grams/Period | Monoethyl m-Toluidine | | Diethyl m-Toluidine | | MEMT + DEMT Prod'ty lb/ft³-hr. | MEMT/ DEMT, Wt. Ratio |
|---|---|---|---|---|---|---|---|---|---|---|---|---|---|---|---|
| | | | | | MT | EA | $H_2O$ | | | Conv. % | Yield % | Conv. % | Yield % | | |
| 1 | 325/334 | 8/8 | 2.0 | 2 | 52.0 | 44.7 | 3.3 | 865 | 831 | 50 | 79 | 10 | 16 | 54 | 4.2 |
| 2 | 325/334 | 8/16 | 2.0 | 2 | 52.0 | 44.7 | 3.3 | 865 | 849 | 51 | 79 | 11 | 17 | 58 | 3.7 |
| 3 | 325/334 | 8/24 | 2.0 | 2 | 52.0 | 44.7 | 3.3 | 862 | 863 | 50 | 73 | 12 | 18 | 57 | 3.4 |
| 4 | 325/334 | 8/32 | 2.0 | 2 | 52.0 | 44.7 | 3.3 | 864 | 838 | 51 | 75 | 13 | 19 | 60 | 3.3 |
| 5 | 325/334 | 8/40 | 2.0 | 2 | 52.0 | 44.7 | 3.3 | 863 | 838 | 53 | 76 | 14 | 20 | 61 | 3.1 |
| 6 | 325/334 | 8/48 | 2.0 | 2 | 52.0 | 44.7 | 3.3 | 866 | 846 | 52 | 75 | 14 | 20 | 62 | 3.0 |
| 7 | 325/334 | 8/56 | 2.0 | 2 | 52.0 | 44.7 | 3.3 | 868 | 844 | 51 | 72 | 14 | 20 | 60 | 3.0 |
| 8 | 325/334 | 8/64 | 2.0 | 2 | 52.0 | 44.7 | 3.3 | 866 | 845 | 52 | 75 | 14 | 21 | 62 | 3.0 |
| 9 | 325/334 | 8/72 | 2.0 | 2 | 52.0 | 44.7 | 3.3 | 863 | 847 | 52 | 73 | 14 | 20 | 61 | 3.1 |
| 10 | 325/334 | 8/80 | 2.0 | 2 | 52.0 | 44.7 | 3.3 | 865 | 838 | 48 | 65 | 13 | 18 | 57 | 3.0 |
| 11 | 325/334 | 8/88 | 2.0 | 2 | 52.0 | 44.7 | 3.3 | 865 | 843 | 52 | 73 | 16 | 21 | 62 | 2.9 |

Table II-continued

N-Ethylation of m-Toluidine

| Run No. | Temp. °C. Furnace/ Hot Spot | Time, Hr. Period/ Total | C.T. Sec. | Mole Ratio EA/ MT | Feed Comp. Wt. % | | | Feed, Grams/ Period | Product Grams/ Period | Monoethyl m-TOluidine | | Diethyl m-Toluidine | | MEMT + DEMT Prod'ty lb/ft³-hr. | MEMT/ DEMT, Wt. Ratio |
|---|---|---|---|---|---|---|---|---|---|---|---|---|---|---|---|
| | | | | | MT | EA | H₂O | | | Conv. % | Yield % | Conv. % | Yield % | | |
| 12 | 325/334 | 8/96 | 2.0 | 2 | 52.0 | 44.7 | 3.3 | 864 | 840 | 52 | 73 | 14 | 20 | 62 | 2.9 |
| 13 | 325/334 | 8/104 | 2.0 | 2 | 52.0 | 44.7 | 3.3 | 864 | 840 | 54 | 75 | 15 | 21 | 64 | 2.9 |
| — | 325/334 | 8/112 | Temperature upset — dropped to 150° C. — Cuts discarded | | | | | | | | | | | | |
| 14 | 325/334 | 8/120 | 2.0 | 2 | 52.0 | 44.7 | 3.3 | 864 | 841 | 51 | 71 | 15 | 21 | 62 | 2.8 |
| 15 | 325/335 | 8/128 | 2.0 | 2 | 52.0 | 44.7 | 3.3 | 861 | 844 | 52 | 71 | 15 | 21 | 61 | 2.8 |
| 16 | 310/320 | 8/136 | 2.0 | 2 | 52.0 | 44.7 | 3.3 | 866 | 848 | 48 | 73 | 13 | 20 | 57 | 3.0 |
| 17 | 310/320 | 8/144 | 2.0 | 2 | 52.0 | 44.7 | 3.3 | 862 | 847 | 46 | 69 | 13 | 19 | 55 | 2.9 |
| 18 | 310/320 | 8/152 | 2.0 | 2 | 52.0 | 44.7 | 3.3 | 863 | 850 | 48 | 74 | 13 | 20 | 56 | 3.0 |
| 19 | 310/320 | 8/160 | 2.0 | 2 | 52.0 | 44.7 | 3.3 | 864 | 855 | 47 | 72 | 13 | 20 | 55 | 3.0 |
| 20 | 310/320 | 8/168 | 2.0 | 2 | 52.0 | 44.7 | 3.3 | 864 | 853 | 46 | 70 | 13 | 19 | 54 | 3.0 |
| 21 | 310/320 | 8/176 | 2.0 | 2 | 52.0 | 44.7 | 3.3 | 865 | 845 | 48 | 76 | 13 | 21 | 57 | 3.1 |
| 22 | 310/320 | 8/184 | 2.0 | 2 | 52.0 | 44.7 | 3.3 | 865 | 850 | 47 | 73 | 13 | 20 | 56 | 3.0 |

The invention has been described in detail with particular reference to certain preferred embodiments thereof, but it will be understood that variations and modifications can be effected within the spirit and scope of the invention.

I claim:

1. A process for the production of N-alkylated aromatic amines which comprises contacting a reaction mixture of an aliphatic alcohol having 1 to about 6 carbon atoms and an aromatic amine having at least 1 hydrogen atom attached to the amino nitrogen, in the vapor phase at a temperature of from about 250° C. to about 450° C. in the presence of a catalyst consisting of eta-alumina treated with hydrofluosilicic acid.

2. The process of claim 1 wherein the alcohol is selected from methyl alcohol and ethyl alcohol, and the aromatic amine is selected from aniline and m-toluidine.

3. The process of claim 2 wherein the alcohol is ethyl alcohol and the aromatic amine is m-toluidine.

4. The process of claim 3 wherein the reaction is carried out at a temperature of from about 275° C. to about 350° C.

* * * * *